US006533873B1

(12) United States Patent
Margosiak et al.

(10) Patent No.: US 6,533,873 B1
(45) Date of Patent: Mar. 18, 2003

(54) SUSPENDING CLEAR CLEANSING FORMULATION

(75) Inventors: Marion Louise Margosiak, Hamden, CT (US); Michael Alan Rahn, New York, NY (US); Rosa Paredes, Shelton, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 96 days.

(21) Appl. No.: 09/630,634

(22) Filed: Aug. 1, 2000

Related U.S. Application Data

(60) Provisional application No. 60/153,355, filed on Sep. 10, 1999.

(51) Int. Cl.[7] ............... C11D 1/65; C11D 3/37; A61K 7/075; A61K 7/48; B08B 3/04
(52) U.S. Cl. ............... 134/42; 134/39; 134/40; 424/70.12; 424/70.16; 424/70.19; 424/70.21; 424/70.24; 424/70.28; 510/121; 510/122; 510/123; 510/127; 510/139; 510/157; 510/158; 510/159
(58) Field of Search ............... 510/121, 122, 510/123, 127, 139, 157, 158, 159, 426, 466; 424/70.12, 70.16, 70.19, 70.21, 70.24, 70.28; 134/39, 40, 42

(56) References Cited

U.S. PATENT DOCUMENTS

| 3,759,861 A | 9/1973 | Shimokawa | 260/31.4 R |
|---|---|---|---|
| 4,552,685 A | 11/1985 | Kernstock et al. | 252/355 |
| 4,591,610 A | 5/1986 | Grollier | 524/55 |
| 4,717,498 A | 1/1988 | Maxon | 252/174.15 |
| 4,849,127 A | 7/1989 | Maxon | 252/174.15 |
| 5,085,857 A | * 2/1992 | Reid et al. | 424/70 |
| 5,415,810 A | 5/1995 | Lee et al. | 252/545 |
| 5,656,257 A | 8/1997 | Fealy et al. | 424/70.13 |
| 6,022,836 A | 2/2000 | Dubief et al. | 510/122 |

FOREIGN PATENT DOCUMENTS

| EP | 0 741 558 B1 | 7/1998 | |
|---|---|---|---|
| GB | 2 283 754 A | 5/1995 | |
| GB | 2283754 A | * 5/1995 | A61K/7/50 |
| WO | 98/13022 | 4/1998 | |
| WO | 99/36054 | 7/1999 | |
| WO | 01/76552 | 10/2001 | |

OTHER PUBLICATIONS

International Search Report PCT/EP 00/08265 dated Jan. 2, 2001 (4 pages).

* cited by examiner

Primary Examiner—Yogendra N. Gupta
Assistant Examiner—Brian P. Mruk
(74) Attorney, Agent, or Firm—Alan A. Bornstein

(57) ABSTRACT

A shower gel formulation having a clear appearance is described which suspends insoluble particles, water insoluble liquids or bubbles and contains an acrylate copolymer, an anionic surfactant, a cationic polymer and, optionally, an amphoteric surfactant. The method of use of the clear shower gel is also described.

15 Claims, No Drawings

SUSPENDING CLEAR CLEANSING FORMULATION

This application claims the benefit of U.S. Provisional Application No. 60/153,355 filed Sep. 10, 1999.

FIELD OF THE INVENTION

The invention relates to a shower gel formulation.

BACKGROUND

Description of the Related Art

Shower gel formulations which are mild to the skin are well known in the art. Such a formulation may optionally contain skin feel agents, such as cationic polymers. However, when one design is to suspend particulates and/or beads in the formulation, frequently substantial quantities of anionic surfactants have been incorporated and provide clear solutions. Unfortunately, the addition of such anionic surfactants diminishes the mildness of the shower gel formulation. U.S. Pat. No. 5,656,257 (Fealy et al., issued on Aug. 12, 1997), which is here incorporated by reference, discloses an anionic shampoo and conditioning composition comprising an oily conditioning agent, a shampooing agent, and an acrylate copolymer, a cationic conditioning agent and water. In this formulation, the acrylate copolymer is used to suspend the anionic shampooing and cationic conditioning agent and prevent it then from inactivating one another. U.S. Pat. No. 5,656,257 does not, however, disclose a clear, mild cleansing composition containing a combination of surfactant types, which is capable of suspending beads or other insoluble particulates or gas bubbles. U.S. Pat. No. 4,552,685 (Kernstock et al., issued Nov. 12, 1985), which is here incorporated by reference, discloses examples of useful acrylate polymers and copolymers capable of thickening mild cleansing agents containing amphoteric surfactants and betaines. However, there is no disclosure regarding the compatability of cationic polymer conditioning agents in the formulation nor the suspending power of the solution for insoluble beads, particulates or gaseous bubbles.

U.S. Pat. No. 3,759,861 (Shimokawa, issued Sep. 18, 1973), which is here incorporated by reference, discloses a clear polymer adhesive complex of an acrylate containing polymer and surfactant used to produce a flocculant. However, there is no disclosure of a shower gel or other cleansing composition containing a cationic conditioning agent or complex which can suspend particulates or gas bubbles.

SUMMARY OF THE INVENTION

The present invention comprises a shower gel formulation having a clear appearance and which suspends beads (e.g. agar/TiO2/sunflower oil beads) insoluble particles and gas bubbles while having one or more acrylate copolymers, a betaine, or other amphoteric surfactant and a cationic polymer (e.g. guar) present in the formulation. It is known that anionic acrylates (i.e. Aculyn type acrylates (available from ISP)) being anionic polymers are generally considered to be incompatible with cationic charged ingredients. It is further known that polymeric cationics, as well as some large, bulky quaternary materials, can possibly be incorporated in formulations containing such acrylates. The optimum order of addition in these instances generally requires the acrylate to be neutralized with a base prior to the addition of any cationics. Applicants have discovered that a clear or transparent product can be produced by either partially neutralizing such acrylates prior to cationic addition or after cationic addition. Clarity or transparency is herein defined as having a turbidity less than or equal to 105 NTU (Nephelometric Turbidity Units).

Applicants have further discovered that amphoteric surfactants, such as Betaine (which is also cationic in nature and not a true amphoteric), may be optionally added to the inventive formulation in the range of 0.01–15 weight percent, preferably 1–10 weight percent to increase mildness without creating noticeable haziness. Prior art shower gels that suspend beads or particulate matter are primarily composed of anionic surfactant and structurant which in most cases are harsher than the inventive formula.

DETAILED DESCRIPTION OF THE INVENTION

In one embodiment, the present invention provides an aqueous, clear shower gel which is capable of suspension, comprising:

About 10–20 weight percent of at least one anionic surfactant;

About 2–15 weight percent of at least one betaine or other amphoteric surfactant;

About 2–15 weight percent of at least one acrylate copolymer;

About 0.05–2 weight percent of at least one cationic polymer;

About 0.1–5 weight percent of beads or particulates;

About 0.1–5 weight percent of a benefit agent such as a water soluble or dispersible silicone polymer;

About 0.1–2 weight percent of a preservative such as a biocide;

In another embodiment, the present invention provides an aqueous, clear cleansing gel which is capable of suspending insoluble material or gas bubbles, comprising:

a. about 5 to 30, preferably 8 to 20 weight percent of at least one anionic surfactant;

b. about 2 to 15, preferably 2 to 10 weight percent of at least one amphoteric surfactant;

c. about 0.1 to 10, preferably 0.5 to 5 weight percent of at least one acrylate copolymer;

d. about 0.01 to 5, preferably 0.1 to 2 weight percent of at least one cationic polymer;

e. about 0.01 to 5, preferably 0.05 to 3 weight percent of at least one insoluble component selected from the group consisting of beads, particulates, water insoluble liquids and gas bubbles;

f. about 50 to 85 weight percent of water g. about 1.9:1 to 15:1, preferably 1.9:1 to 10:1 weight percent ratio range of anionic surfactant to amphoteric surfactant;

h. about 0.1:1 to 15:1, preferably 0.3:1 to 10:1, weight percent ratio range of the sum of cationic polymer and amphoteric surfactant to acrylate copolymer; and wherein the concentration of acrylate copolymer is sufficient to suspend said at least one insoluble component, preferably wherein the viscosity range is between 6,000 and 20,000 cps, and the pH is in the range of 5.5 to 7.0.

In a further embodiment, the present invention provides an aqueous, clear cleansing gel which is capable of suspending insoluble material or gas bubbles, comprising:

a. about 5 to 30, preferably 8 to 20 weight percent of at least one anionic surfactant;

b. about 0.1 to 10, preferably 0.5 to 5 weight percent of at least one acrylate copolymer;

c. about 0.01 to 5, preferably 0.1 to 2 weight percent of at least one cationic polymer;
d. about 0.01 to 5, preferably 0.05 to 3 weight percent of at least one insoluble component selected from the group consisting of beads, particulates, water insoluble liquids and gas bubbles;
e. about 50 to 85 weight percent of water; and
wherein the concentration of acrylate copolymer is sufficient to suspend said at least one insoluble component, preferably wherein the viscosity range is between 6,000 and 20,000 cps, and the pH is in the range of 5.5 to 7.0.

Amonic surfactants, foam boosters, amphoteric and zwitterionic surfactants, which are useful in the present invention, are described in U.S. Pat. No. 5,221,530, issued to Janchitraponvej et al. on Jun. 22, 1993, which is herein incorporated by reference.

Acrylate polymers and copolymers which are useful in the invention include one or more copolymers containing at least one monomer selected from the group consisting of methacrylic acid, acrylic acid, amino acrylic acid, an acrylic acid ester of a C8–30 alkyl, alkylaryl, aryl, heterocyclic, alkoxyl, alkoxyl alkyl ester of a C8–30 alkyl or alkenyl; either substituted or unsubstituted; a methacrylic acid ester of a C8–C30 alkyl, alkylaryl, aryl, heterocyclic, alkoxyl, alkoxyl alkyl ester of a C8–30 alkyl, or alkenyl; either substituted or unsubstituted; a C1–4 alkyl acrylate, and a C1–4 methacrylate; either substituted or unsubstituted, and the like. Other useful acrylate polymers and copolymers are disclosed in U.S. Pat. No. 5,656,257.

Preferred acrylate polymers include the following INCI Named materials: acrylates/c12–24 pareth-25 acrylate copolymer, obtainable as Synthalen® W2000 from 3V Inc. (Wehawken, N.J.); acrylates/steareth-20 methacrylate copolymer obtainable as Aculyn® 22 from International Specialty Products Corp. (Lombard, Ill.); and acrylates copolymer obtainable as either Aculyn® 33 from International Specialty Products Corp. or as Polymer EX-518® from BF Goodrich Corp. (Brecksville, Ohio); acrylates/steareth-20 itaconate copolymer, obtainable as Structure 2001®; acrylates/ceteth-20 itaconate copolymer, obtainable as Structure 3001®; and acrylates/aminoacrylates/C10–30 alkyl PEG-20 itaconate copolymer, obtainable as Structure Plus® all from National Starch & Chemical, Inc. (Bridgewater, N.J.), and the like.

The inventive compositions may be used for the cleansing of the user's skin and hair and is applied to a surface (e.g. a skin surface) via topical applications to release or deposit an effective amount of the transparent composition to perform the desired cleansing function. The frequency of topical application can vary widely, depending on the user's need. With respect to personal application to the skin, such application can range from about once per day to about four times per day, preferably from about twice a day to about three times a day.

The following examples are intended to illustrate the invention and not limit the invention in any way.

Several inventive transparent shower gels with suspended insoluble particles were prepared and compared to comparative shower gels that did not display clarity. The compositions of these shower gels are summarized in Table 1 and 2. The processing methods used to prepare these compositions are listed in table 1 and are provided below:

TABLE 1

| Ingredients | Ex. 1 % wt/wt | Ex. 2 % wt/wt | Ex. 3 % wt/wt | Ex. 4 % wt/wt | Ex. 5 % wt/wt | Ex. 6 % wt/wt | Ex. 7 % wt/wt |
|---|---|---|---|---|---|---|---|
| Sodium Laureth Sulfate | 11.0 | 13.0 | 11.0 | 10.0 | 11.0 | 11.0 | 7.0 |
| Cocamidopropyl betaine | 6.0 | | 3.0 | 2.1 | 3.0 | 3.0 | 6.0 |
| Acrylates Copolymer | 1.8 | 2.0 | 1.5 | | 3.0 | | 1.8 |
| Acrylates/C12–24 Pareth-25 Acrylate Copolymer | | | | 3.0 | | | |
| Acrylates/Steareth-20 Methacrylate copolymer | 1.25 | 0.5 | | | 0.5 | | 1.0 |
| Acrylates/Steareth-20 Itaconate Copolymer | | | | | | | |
| Acrylates/Ceteth-20 Itaconate Copolymer | | | | | | | |
| Acrylates/Aminoacrylates Copolymer | | | | | | 2.18 | |
| Disodium Dimethicone Copolyol Sulfosuccinate | 0.15 | 0.25 | 0.15 | | 0.15 | 0.15 | 0.15 |
| Fragrance | | 0.86 | 0.86 | | | | |
| Polyquaternium-22 | | | | | | | 0.2 |
| Polyquaternium-10 | | | | | | | |
| Hydroxypropyl Guar Hydroxypropyl Trimonium Chloride | 0.1 | 0.2 | 0.2 | | 0.1 | 0.1 | |
| Ammonium Sulfate | | | | 0.6 | | | |
| Propylene Glycol | 2.0 | 0.5 | 0.5 | | 1.0 | 0.5 | |
| DMDM Hydantoin + IPBC | 0.22 | | | 0.22 | | 0.22 | 0.22 |
| Methylchloroisothiazolinone (and) Methylisothiazolinone | | 0.0003 | 0.0003 | | 0.0004 | | |
| Sodium Hydroxide | 0.5 | 0.5 | 0.25 | 0.75 | 1.0 | | 0.5 |
| Citric Acid | | | | | | 0.5 | |
| Insoluble components | 0.5 | 0.05 | 0.05 | 0.5 | 0.05 | 0.5 | 0.5 |
| Tetrasodium EDTA | 0.05 | 0.02 | | | 0.02 | 0.05 | 0.05 |
| Etidronic Acid | | 0.02 | | | 0.02 | | |

TABLE 1-continued

| | Ex. 1 % wt/wt | Ex. 2 % wt/wt | Ex. 3 % wt/wt | Ex. 4 % wt/wt | Ex. 5 % wt/wt | Ex. 6 % wt/wt | Ex. 7 % wt/wt |
|---|---|---|---|---|---|---|---|
| Benzophenone-4 | | 0.2 | | | 0.2 | | |
| Glycerin USP | | 0.5 | 0.5 | | 0.5 | | |
| Water | q.s. to 100 | q.s. to 100 | q.s. to 100 | q.s. to 100 | q.s. to 100 | q.s. to 100 | q.s. to 100 |
| Processing Method | 6 | 8 | 1 | 4 | 5 | 2 | 7 |
| Turbidity Test | FAIL | PASS | PASS | PASS | PASS | PASS | FAIL |
| Category | C | I | I | I | I | I | C |

| Ingredients | Ex. 8 % wt/wt | Ex. 9 % wt/wt | Ex. 10 % wt/wt | Ex. 11 % wt/wt | Ex. 12 % wt/wt | Ex. 13 % wt/wt | Ex. 14 % wt/wt |
|---|---|---|---|---|---|---|---|
| Sodium Laureth Sulfate | 11.0 | 11.0 | 20.0 | 11.0 | 11.0 | 11.0 | 11.0 |
| Cocamidopropyl betaine | 3.0 | 3.0 | 6.0 | 3.0 | 3.0 | 3.0 | 6.0 |
| Acrylates Copolymer | | 2.0 | 4.0 | | | 2.0 | 1.8 |
| Acrylates/C12–24 Pareth-25 Acrylate Copolymer | 1.75 | | | | | | |
| Acrylates/Steareth-20 Methacrylate copolymer | | 0.5 | 1.0 | | | 0.5 | 1.0 |
| Acrylates/Steareth-20 Itaconate Copolymer | | | | 5.0 | | | |
| Acrylates/Ceteth-20 Itaconate Copolymer | | | | | 5.0 | | |
| Acrylates/Aminoacrylates Copolymer | | | | | | | |
| Disodium Dimethicone Copolyol Sulfosuccinate | 0.15 | 0.15 | 0.15 | 0.15 | 0.15 | 0.25 | 0.15 |
| Fragrance | 0.86 | 0.86 | 0.86 | | | | |
| Polyquaternium-22 | | | | | | | 0.2 |
| Polyquaternium-10 | | | | | | 0.2 | |
| Hydroxypropyl Guar Hydroxypropyl Trimonium Chloride | 0.2 | 0.1 | 0.1 | 0.1 | 0.1 | | |
| Ammonium Sulfate | 1.5 | 0.25 | | | | | |
| Propylene Glycol | 1.0 | 0.5 | 1.5 | 5.0 | 1 | 2.7 | 1.0 |
| DMDM Hydantoin + IPBC | | | 0.22 | 0.22 | 0.22 | | 0.22 |
| Methylchloroisothiazolinone (and) Methylisothiazolinone | 0.0003 | 0.0003 | | | | 0.0003 | |
| Sodium Hydroxide | 0.5 | 1.0 | 1.0 | 0.5 | 0.5 | 0.4 | 0.5 |
| Citric Acid | | | | | | | |
| Insoluble components | 0.05 | 0.05 | 0.5 | 0.5 | 0.5 | 0.05 | 0.05 |
| Tetrasodium EDTA | | 0.02 | | 0.05 | 0.05 | 0.02 | |
| Etidronic Acid | | 0.02 | | | | 0.02 | |
| Benzophenone-4 | | 0.2 | | | | 0.2 | |
| Glycerin USP | 0.05 | 0.5 | | | | 0.5 | |
| Water | q.s. to 100 | q.s. to 100 | q.s. to 100 | q.s. to 100 | q.s. to 100 | q.s. to 100 | q.s. to 100 |
| Processing Method | 1 | 3 | 9 | 10 | 10 | 5 | 11 |
| Turbidity Test | PASS | PASS | PASS | PASS | PASS | PASS | FAIL |
| Category | I | I | I | I | I | I | C |

Note: I is inventive and C is comparative

Method 1

The initial distilled water charge is added to a center turbine tank with wall scrape agitation and heated to 165° F. Maintain 165° F. Increase agitation of the center turbine and the wall sweep so that there is a slight vortex. Add acrylate copolymer to the tank and mix. The anionic surfactants are added to the tank and mixed and then the amphoteric surfactant is added and mixed. Premix the cationic polymer with propylene glycol if the cationic polymer is a solid, and mix well with no lumps. If the cationic polymer is a liquid, add straight to the tank. Add the glycerin. Decrease agitation and mix for 30 minutes at 165° F. and then start to cool to 95° F. During the cooling process, measure the pH and adjust with an alkaline pH adjuster to clarity within a target pH range of 5.5 to 7.0. At 115° F., add the preservative and at 105° F. add the fragrance and mix well. Cool to 95° F. At 95° F, measure the viscosity and adjust with ammonium sulfate to the desired viscosity. Add the insoluble components and mix gently. Cool to room temperature.

Method 2

The initial distilled water charge is added to a center turbine tank with wall scrape agitation and heated to 165° F. Maintain 165° F. Increase agitation of the center turbine and the wall sweep so that there is a slight vortex. Add tetrasodium EDTA to the tank and mix. Premix the cationic polymer with propylene glycol if the cationic polymer is a solid, and mix well with no lumps. If the cationic polymer is a liquid, add straight to the tank. Add anionic surfactants and mix. Add amphoteric surfactants and mix. Add the acrylate copolymer and mix. Mix for 30 minutes at 165° F and then start to cool to 95° F. At 115° F., add the preservative and mix well. At 95° F., measure the pH and adjust with citric acid to clarity within a target pH range of 5.5 to 7.0. At 95° F., measure the viscosity and adjust if necessary to the desired viscosity. Add the insoluble components and mix. Cool to room temperature.

Method 3

The initial distilled water charge is added to a center turbine tank with wall scrape agitation and heated to 165° F.

Maintain 165° F. Increase agitation of the center turbine and the wall sweep so that there is a slight vortex. The acrylate copolymer is added to the tank and mixed. The anionic surfactant is added and mixed. Decrease agitation and add the amphoteric surfactant and mix. Premix the cationic polymer with propylene glycol if the cationic polymer is a solid, and mix well with no lumps. If the cationic polymer is a liquid, add straight to the tank. Premix the remaining acrylate copolymer with water to a dilution of 4.5 to 1 and add to the tank and mix with gentle agitation. Mix the batch for 30 minutes at 165° F. and start to cool to 95° F. At 120° F., add the glycerin, at 115° F, add the preservative and then the UV inhibitor. At 110° F., add the EDTA and the EHDP and at 105° F., add the fragrance and mix. At 95° F., measure the pH and adjust with an alkaline pH adjuster to clarity within a target pH range of 5.9 to 7.0. At 95° F., measure the viscosity and adjust with propylene glycol to the desired viscosity. Add the insoluble components and mix gently. Cool to room temperature.

Method 4

The initial distilled water charge is added to a center turbine tank with wall scrape agitation and heated to 115° F. Maintain 115° F. Increase agitation of the center turbine and the wall sweep so that there is a slight vortex. Add preservative to the tank and mix. Add the acrylate copolymer to the tank slowly and mix for 5 minutes. Add the anionic surfactants, then the amphoteric surfactants and mix. Cool the batch to 95° F. At 95° F., measure the pH and adjust with an alkaline pH adjuster to a target pH range of 5.5 to 7.0. At 95° F., measure the viscosity and adjust with propylene glycol to the desired viscosity. Add the insoluble components and mix. Cool to room temperature.

Method 5

The initial distilled water charge is added to a center turbine tank with wall scrape agitation and heated to 165° F. Maintain 165° F. Increase agitation of the center turbine and the wall sweep so that there is a slight vortex. The acrylate copolymer is added to the tank and mixed. The anionic surfactant is added and mixed. Decrease agitation and add the amphoteric surfactant and mix. Premix the cationic polymer with propylene glycol if the cationic polymer is a solid, and mix well with no lumps. If the cationic polymer is a liquid, add straight to the tank. Premix the remaining acrylate copolymer with water to a dilution of 4.5 to 1 and add to the tank and mix with gentle agitation. Mix the batch for 30 minutes at 165° F. and start to cool to 95° F. At 120° F., add the glycerin, at 115° F., add the preservative and then the UV inhibitor. At 110° F., add the EDTA and the EHDP and mix. At 95° F., measure the pH and adjust with an alkaline pH adjuster to clarity within a target pH range of 5.9 to 7.0. At 95° F., measure the viscosity and adjust with propylene glycol to the desired viscosity. Add the insoluble components and mix gently. Cool to room temperature.

Method 6

The initial distilled water charge is added to a center turbine tank with wall scrape agitation and heated to 165° F. Maintain 165° F. Increase agitation of the center turbine and the wall sweep so that there is a slight vortex. Add tetrasodium EDTA to the tank. Premix the cationic polymer with propylene glycol if the cationic polymer is a solid, and mix well with no lumps. If the cationic polymer is a liquid, add straight to the tank. Decrease agitation and add the acrylate copolymer(s) and mix. Add the anionic surfactants to the tank and mix. The amphoteric surfactant is added next and mixed. Mix for 30 minutes at 165° F. and then start to cool to 95° F. At 115° F., add the preservative and mix well. At 95° F., measure the pH and adjust with an alkaline pH adjuster to clarity within a target pH range of 5.5 to 7.0. At 95° F., measure the viscosity and adjust with propylene glycol to the desired viscosity. Add the insoluble components and mix. Cool to room temperature.

Method 7

The initial distilled water charge is added to a center turbine tank with wall scrape agitation and heated to 165° F. Maintain 165° F. Increase agitation of the center turbine and the wall sweep so that there is a slight voilex. Add tetrasodium EDTA to the tank and then the acrylate copolymer(s). Add the anionic surfactants to the tank and mix. The amphoteric surfactant is added next and mixed. Premix the cationic polymer with propylene glycol if the cationic polymer is a solid, and mix well with no lumps. If the cationic polymer is a liquid, add straight to the tank. Decrease agitation and mix for 30 minutes at 165° F. and then start to cool to 95° F. At 115° F., add the preservative and mix well. At 95° F., measure the pH and adjust with an alkaline pH adjuster to clarity within a target pH range of 5.5 to 7.0. At 95° F., measure the viscosity and adjust with propylene glycol to the desired viscosity. Add the insoluble components and mix. Cool to room temperature.

Method 8

The initial distilled water charge is added to a center turbine tank with wall scrape agitation and heated to 165° F. Maintain 165° F. Increase agitation of the center turbine and the wall sweep so that there is a slight vortex. The acrylate copolymer is added to the tank and mixed. The anionic surfactant is added and mixed. Decrease agitation and add the amphoteric surfactant and mix. Premix the cationic polymer with propylene glycol if the cationic polymer is a solid, and mix well with no lumps. If the cationic polymer is a liquid, add straight to the tank. Premix the remaining acrylate copolymer with water to a dilution of 4.5 to 1 and add to the tank and mix with gentle agitation. Mix the batch for 30 minutes at 165° F. and start to cool to 95° F. At 120° F., add the glycerin, at 115° F., add the preservative and then the UV inhibitor. At 110° F., add the EDTA and the EHDP and mix. At 105° F., add the fragrance and mix well. At 95° F., measure the pH and adjust with an alkaline pH adjuster to clarity within a target pH range of 5.9 to 7.0. At 95° F., measure the viscosity and adjust with propylene glycol to the desired viscosity. Add the insoluble components and mix. Cool to room temperature.

Method 9

The initial distilled water charge is added to a center turbine tank with wall scrape agitation and heated to 165° F. Maintain 165° F. Increase agitation of the center turbine and the wall sweep so that there is a slight vortex. The acrylate copolymer is added to the lank and mixed. The anionic surfactant is added and mixed. Decrease agitation and add the amphoteric surfactant and mix. Premix the cationic polymer with propylene glycol if the cationic polymer is a solid, and mix well with no lumps. If the cationic polymer is a liquid, add straight to the tank. Premix the remaining acrylate copolymer with water to a dilution of 4.5 to 1 and add to the tank and mix with gentle agitation. Mix the batch for 30 minutes at 165° F. and start to cool to 95° F. At 115° F., add the preservative, at 105° F., add the fragrance and mix. At 95° F., measure the pH and adjust with an alkaline pH adjuster to clarity within a target pH range of 5.9 to 7.0. At 95° F., measure the viscosity and adjust with propylene glycol to the desired viscosity. Add the insoluble components and mix gently. Cool to room temperature.

Method 10

The initial distilled water charge is added to a center turbine tank with wall scrape agitation and heated to 165° F.

Maintain 165° F. Increase agitation of the center turbine and the wall sweep so that there is a slight vortex. Add EDTA to the tank and mix. Premix the cationic polymer with propylene glycol if the cationic polymer is a solid, and mix well with no lumps. If the cationic polymer is a liquid, add straight to the tank. The anionic surfactant is added and mixed. The amphoteric surfactant is added and mixed. The acrylate copolymer is added to the tank and mixed. Decrease the agitation and mix the batch for 30 minutes at 165° F. and then start to cool to 95° F. At 115° F., add the preservative and mix. At 95° F, measure the pH and adjust with an alkaline pH adjuster to clarity within a target pH range of 5.9 to 7.0. At 95° F., measure the viscosity and adjust with propylene glycol to the desired viscosity. Add the insoluble components and mix. Cool to room temperature.

Method 11

The initial distilled water charge is added to a center turbine tank with wall scrape agitation and heated to 165° F. Maintain 165° F. Increase agitation of the center turbine and the wall sweep so that there is a slight vortex. Add EDTA to the tank and then the acrylate copolymers and mix. The anionic surfactant is added and mixed. The amphoteric surfactant is added and mixed. Premix the cationic polymer with propylene glycol if the cationic polymer is a solid, and mix well with no lumps. If the cationic polymer is a liquid, add straight to the tank. Decrease the agitation and mix the batch for 30 minutes at 165° F. and then start to cool to 95° F. At 115° F., add the preservative and mix. At 95° F., measure the pH and adjust with an alkaline pH adjuster to clarity within a target pH range of 5.9 to 7.0. At 95° F., measure the viscosity and adjust with propylene glycol to the desired viscosity. Add the insoluble components and mix. Cool to room temperature.

EXAMPLE 15

The following is another example of the invention.

TABLE 2

| Ingredient | % by weight |
|---|---|
| Anionic surfactant (e.g. Sodium Laureth Sulfate (3EO) | About 10–20 |
| Betaine (e.g. Cocoamidopropyl betaine) | About 2–15 |
| Acrylate Copolymer (e.g. Aculyn 33 and 22) | About 2–15 |
| Silicone (e.g. Dimethicone Copolyol Sulfosuccinate | About 0.1–5 |
| Fragrance | About 0–1.0 |
| Cationic surfactant (e.g.- Hydroxypropyl Guar Hydroxypropyl Trimonium Chloride) | About .05–5 |
| Propylene Glycol | About 0.1–2.0 |
| Preservative | About 0.1–2.0 |
| Sodium Hydroxide | to adjust pH to 6.0 to 7.0 |
| Beads (e.g. Agar/Titanium Dioxide/Sunflower Oil Beads | About 0.1–2.0 |
| Water | q.s. to 100 |

Methods

Viscosity

For the purposes of this invention, viscosity is measured using conventional techniques with a Brookfield viscometer, Model HBDVII+ CP, spindle No. 41 at 0.5 rpm at 25° C.

Turbidity

For the purposes of this invention, the acceptability of formulation clarity was measured qualitatively and quantitively using a visual method of turbidity determination and a turbidimeter respectively. Briefly, the visual method involves looking through a determined path length of the formulation to a visual target and determining if the visual target is legible or recognizable. This target may be a straight line, a set of parallel lines, a number or a letter printed on white paper. Place test formulation in a glass beaker such that the height from the bottom of the beaker to the top surface of the formulation is four inches. Make sure the formulation is free of air bubbles. Place the piece of paper with the visual target under the beaker. Look through the top surface of the formulation to the visual target. If the visual target appears similar to the original, the formulation is of acceptable clarity and receives a 'pass' rating. If the visual target appears significantly hazy, or is out of focus, compared to the original target, the formulation is of unacceptable clarity and receives a 'fail' rating.

Turbidity was quantitatively determined by a Turbidimeter, Model DRT-100D, manufactured by Shaban Manufacturing Inc, H. F. Instruments Division using a sample cuvette of 28 mm diameter by 91 mm in length with a flat bottom. Samples that had received a 'pass' rating from the visual method were found to have a turbidity measurement of less than or equal to 105 NTU's (Nephelometric Turbidity Units). Samples that had received a 'fail' rating from the visual method were found to have a turbidity measurement of greater than 105 NTU's.

The foregoing description and examples illustrate selected embodiments of the present invention. In light thereof, variations and modifications will be suggested to one skilled in the art, all of which are written the scope and spirit of this invention.

We claim:

1. A transparent cleansing composition, comprising:
   a. about 5 to 30 weight percent of at least one anionic surfactant;
   b. about 2 to 15 weight percent of at least one amphoteric surfactant;
   c. about 0.1 to 10 weight percent of at least one acrylate copolymer;
   d. about 0.01 to 5 weight percent of at least one cationic polymer;
   e. about 0.01 to 5 weight percent of at least one insoluble component selected from the group consisting of beads, particulates, water insoluble liquids and gas bubbles;
   f. about 50 to 85 weight percent of water
   g. about 1.9:1 to 15:1 weight percent ratio range of anionic surfactant to amphoteric surfactant;
   h. about 0.1:1 to 15:1 weight percent ratio range of the sum of cationic polymer and amphoteric surfactant to acrylate copolymer; and
      wherein the concentration of acrylate copolymer is sufficient to suspend said at least one insoluble component.

2. The cleansing composition of claim 1, comprising:
   a. about 8 to 20 weight percent of at least one anionic surfactant;
   b. about 2 to 10 weight percent of at least one amphoteric surfactant;
   c. about 0.5 to 5 weight percent of at least one acrylate copolymer;
   d. about 0.1 to 2 weight percent of at least one cationic polymer;

e. about 0.05 to 3 weight percent of at least one insoluble component selected from the group consisting of beads, particulates, water insoluble liquids and gas bubbles;

f. about 50 to 85 weight percent of water;

g. about 1.9:1 to 10:1 weight percent ratio range of anionic surfactant to amphoteric surfactant;

h. about 0.3:1 to 10:1 weight percent ratio range of the sum of cationic polymer and amphoteric surfactant to acrylate copolymer; and wherein the viscosity range is between 6000 and 20000 cps, and the pH is in the range of 5.5 to 7.0.

3. The cleansing composition of claim 1 wherein said anionic surfactant is selected from the group consisting of alkyl sulfates, alkyl ether sulfates, alkyl sulfonates, alkylbenzene sulfonates, alkyl succinates, alkyl sulfosuccinates, alkyl olefin sulfonates, alkyl sarcosinates, octoxynol phosphates, nonoxynol phosphates, alkyl taurates, polyoxyethylene sulfates, polyoxyethylene isethionates, alkyl carboxylates, and alkyl ether carboxylates.

4. The cleansing composition of claim 1 wherein said amphoteric surfactant is selected from the group consisting of alkyl betaines, alkyl amino betaines, hydroxysultaines, alkyl amphoacetates, and alkylampho carboxyglycinates.

5. The cleansing composition of claim 1 wherein said at least one acrylate copolymer includes one or more copolymers containing at least one monomer selected from the group consisting of methacrylic acid, acrylic acid, amino acrylic acid, an acrylic acid ester of a C8–30 alkyl, alkylaryl, aryl, heterocyclic, alkoxyl, alkoxyl alkyl ester of a C8–30 alkyl or alkenyl; which is either substituted or unsubstituted; a methacrylic acid ester of a C8–C30 alkyl, alkylaryl, aryl, heterocyclic, alkoxyl, alkoxyl alkyl ester of a C8–30 alkyl, or alkenyl; which is either substituted or unsubstituted; a C1–4 alkyl acrylate, and a C1–4 methacrylate; which is either substituted or unsubstituted.

6. The cleansing composition of claim 1 wherein said cationic polymer is selected from the group consisting of quaternized guar gums, quaternized phosphate esters, quaternized polysaccharides or their derivatives, quaternized polyamides, quaternized polymeric derivatives of acrylates, methacrylates, acrylamides, methacrylamides or copolymers thereof, and quaternized polymeric derivatives of substituted allyl or vinyl compounds.

7. The cleansing composition of claim 1 wherein said at least one insoluble component is selected from the group consisting of glass beads, plastic beads, macaroni food products, organic materials, inorganic materials, crystalline solids, oil droplets, vegetable and fruit purees, water insoluble dimethicones, air and gas bubbles.

8. A transparent cleansing composition, comprising:

a. about 5 to 30 weight percent of at least one anionic surfactant;

b. about 0.1 to 10 weight percent of at least one acrylate copolymer;

c. about 0.01 to 5 weight percent of at least one cationic polymer;

d. about 0.01 to 5 weight percent of at least one insoluble component selected from the group consisting of beads, particulates, water insoluble liquids and gas bubbles;

e. about 50 to 85 weight percent of water; and wherein the concentration of acrylate copolymer is sufficient to suspend said at least one insoluble component.

9. The cleansing composition of claim 8, comprising:

a. about 8 to 20 weight percent of at least one anionic surfactant;

b. about 0.5 to 5 weight percent of at least one acrylate copolymer;

c. about 0.1 to 2 weight percent of at least one cationic polymer;

d. about 0.05 to 3 weight percent of at least one insoluble component selected from the group consisting of beads, particulates, water insoluble liquids and gas bubbles;

e. about 50 to 85 weight percent of water; and wherein the viscosity range is between 6000 and 20,000 cps, and the pH is in the range of 5.5 to 7.0.

10. The cleansing composition of claim 8 wherein said anionic surfactant is selected from the group consisting of alkyl sulfates, alkyl ether sulfates, alkyl sulfonates alkylbenzene sulfonates, alkyl succinates, alkylbenzene succinates, alkylbenzene sulfosuccinates, alkyl olefin sulfonates, alkyl sarcosinates, alkyl sulfosuccinates, octoxynol phosphates, nonoxynol phosphates, alkyl taurates, polyoxyethylene sulfates, polyoxyethylene isethionates, alkyl carboxylates, and alkyl ether carboxylates.

11. The cleansing composition of claim 8 wherein said at least one acrylate copolymer includes one or more copolymers containing at least one monomer selected from the group consisting of methacrylic acid, acrylic acid, amino acrylic acid, an acrylic acid ester of a C8–30 alkyl, alkylaryl, aryl, heterocyclic, alkoxyl, alkoxyl alkyl ester of a C8–30 alkyl or alkenyl; which is either substituted or unsubstituted; a methacrylic acid ester of a C8–C30 alkyl, alkylaryl, aryl, heterocyclic, alkoxyl, alkoxyl alkyl ester of a C8–30 alkyl, or alkenyl; which is either substituted or unsubstituted; a C1–4 alkyl acrylate, and a C1–4 methacrylate; which is either substituted or unsubstituted.

12. The cleansing composition of claim 8 wherein said cationic polymer is selected from the group consisting of quaternized guar gums, quaternized phosphate esters, quaternized polysaccharides or polysaccharide derivatives, quaternized polyamides, quaternized polymeric derivatives of acrylates, methacrylates, acrylamides, methacrylamides or copolymers, quaternized polymeric derivatives of substituted allyl or vinyl compounds.

13. The cleansing composition of claim 8 wherein said at least one insoluble component is selected from the group consisting of glass beads, plastic beads, macaroni food products, organic materials, inorganic materials, crystalline solids, oil droplets, vegetable and fruit purees, water insoluble dimethicones, air and gas bubbles.

14. A method of cleaning the skin or hair with a transparent cleansing product comprising:

1. selecting a composition including, a. about 5 to 30 weight percent of at least one anionic surfactant;

b. about 2 to 15 weight percent of at least one amphoteric surfactant;

c. about 0.1 to 10 weight percent of at least one acrylate copolymer;

d. about 0.01 to 5 weight percent of at least one cationic polymer;

e. about 0.01 to 5 weight percent of at least one insoluble component selected from the group consisting of beads, particulates, water insoluble liquids and gas bubbles;

f. about 50 to 85 weight percent of water;

g. about 1.9:1 to 15:1 weight percent ratio range of anionic surfactant to amphoteric surfactant;

h. about 0.1:1 to 15:1 weight percent ratio range of the sum of cationic polymer and amphoteric surfactant to acrylate copolymer; and wherein the concentration of acrylate copolymer is sufficient to suspend said at least one insoluble component;

2. applying the composition to the skin or hair; and 3. rinsing off the composition with water.

15. A method of cleansing the skin or hair with a transparent cleansing product comprising:
1. selecting a composition including,
   a. about 5 to 30 weight percent of at least one anionic surfactant;
   b. about 0.1 to 10 weight percent of at least one acrylate copolymer;
   c. about 0.01 to 5 weight percent of at least one cationic polymer;
   d. about 0.01 to 5 weight percent of at least one insoluble component selected from the group consisting of beads, particulates, water insoluble liquids and gas bubbles;
   e. about 50 to 85 weight percent of water; and
   wherein the concentration of acrylate copolymer is sufficient to suspend said at least one insoluble component;
2. applying the composition to the skin or hair; and
3. rinsing off the composition with water.

* * * * *